US00PP13758P39

(12) United States Plant Patent
Fear

(10) Patent No.: US PP13,758 P3
(45) Date of Patent: May 6, 2003

(54) BLACKBERRY PLANT NAMED 'SLEEPING BEAUTY'

(75) Inventor: Carlos D. Fear, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 66 days.

(21) Appl. No.: 09/772,329

(22) Filed: Jan. 29, 2001

(65) Prior Publication Data

US 2002/0148017 P1 Oct. 10, 2002

(51) Int. Cl.[7] ..... A01H 5/00

(52) U.S. Cl. ..... Plt./203

(58) Field of Search ..... Plt./203

*Primary Examiner*—Bruce R. Campell
*Assistant Examiner*—June Hwu
(74) *Attorney, Agent, or Firm*—Pennie & Edmonds LLP

(57) ABSTRACT

The present invention relates to a new and distinct cultivar of blackberry plant named 'Sleeping Beauty'. The new cultivar is distinguished from other blackberry cultivars by its large fruit, low chill requirement, and long fruiting period. The new cultivar is distinguished from its pollen parent by having an earlier fruiting period and much lower chill requirement. The new cultivar is distinguished from its seed parent by having firmer and less acidic fruit.

3 Drawing Sheets

LATIN NAME OF THE GENUS AND SPECIES OF THE PLANT CLAIMED

Rubus hybrid

VARIETY DENOMINATION

'Sleeping Beauty'

1. BACKGROUND OF THE INVENTION

This invention relates to a new cultivar of blackberry called 'Sleeping Beauty'. The new cultivar was developed from hybridization of the unpatented female cultivar 'Brazos' with the unpatented male cultivar 'Hull Thornless'. The parents were crossed in Spring 1991 whereafter fruit and seed were collected to produce seedlings for field planting in Watsonville, Calif. in 1992. The new cultivar was selected in 1994 for its early fruiting period and large fruit size. The cultivar has been asexually propagated, and reproduced true to type plants by in vitro shoot tip culture.

2. SUMMARY OF THE INVENTION

The present invention provides a new and distinct blackberry cultivar named 'Sleeping Beauty'. The variety is botanically identified as Rubus L. subgenus Rubus. The variety is described as a complex Rubus hybrid. It can be characterized as an erect tetraploid with considerable *R. allegheniensis* background with other species such as *R. trivalis, R. argutus, R. ulmifolius,* and *R. procerus* also appearing in its background. The new cultivar produces a floricane crop which begins in mid-May and continues until mid-August. The new blackberry variety is distinguished from other varieties by a number of characteristics as set forth in Table 1. In particular, the new cultivar is distinguished by its large fruit, low chill requirement and long fruiting period. Yield of the new cultivar is moderate to high when compared to many other varieties. There have been no observed plant or fruit diseases and no observed pest resistance or susceptibility. The variety has been developed for fresh market shipping use, and has performed well in coast-to-coast shipping tests and held up well after cold storage at 34 degrees Fahrenheit for periods of up to ten days.

3. COMPARISON TO SIMILAR VARIETIES

The variety that we believe to be similar to 'Sleeping Beauty' from those known to us is 'Brazos', an unpatented variety. 'Sleeping Beauty' is particularly different from 'Brazos' by having firmer, less acidic fruit and by being slightly smaller in size.

BRIEF DESCRIPTION OF THE DRAWINGS

The accompanying photographs show typical specimens of the fruit, leaves and shoot of the new cultivar, in color as nearly true as reasonably possible in color illustrations of this type.

5. DESCRIPTION OF THE NEW VARIETY

Figure 1:
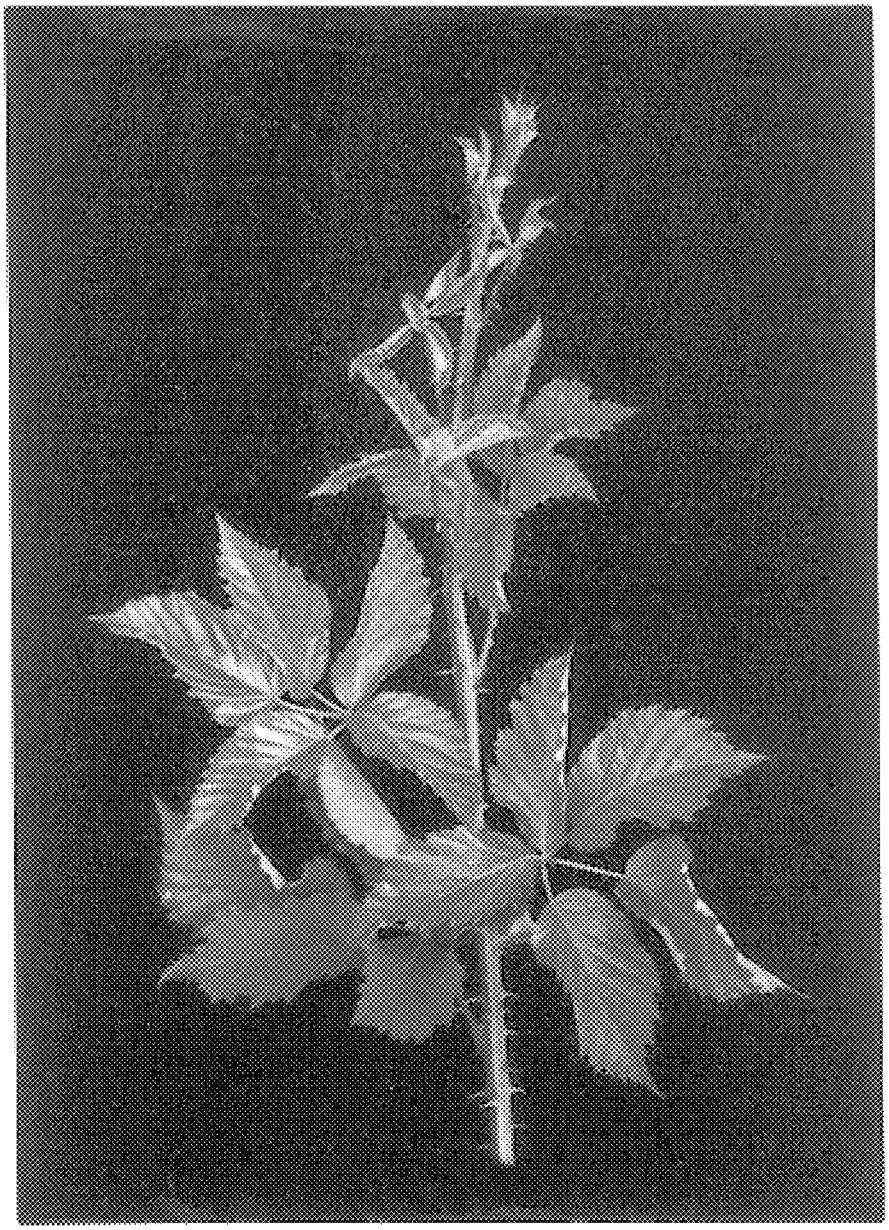
FIG. 1 is a photograph showing a primocane shoot, mature leaf and stem of 'Sleeping Beauty'.
Figure 2:
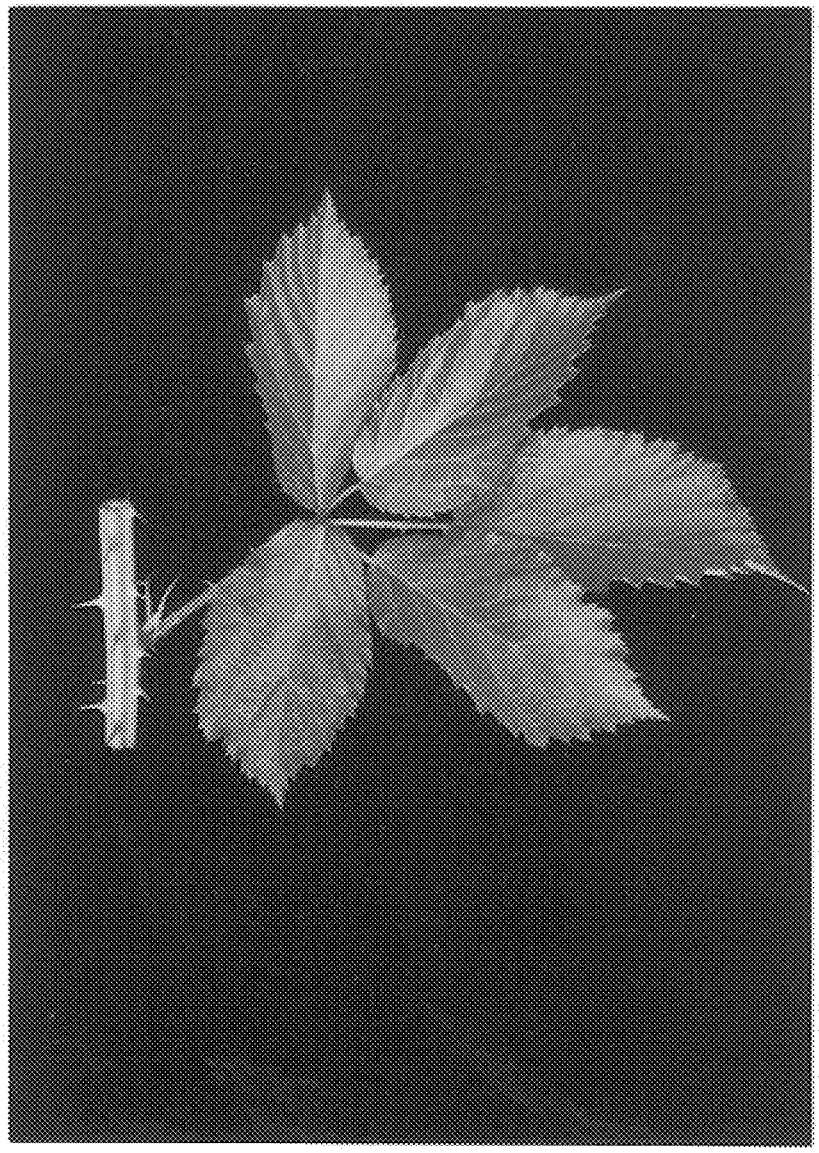
FIG. 2 is a photograph showing a close-up view of a primocane shoot, mature leaf and stem of 'Sleeping Beauty'.
Figure 3:
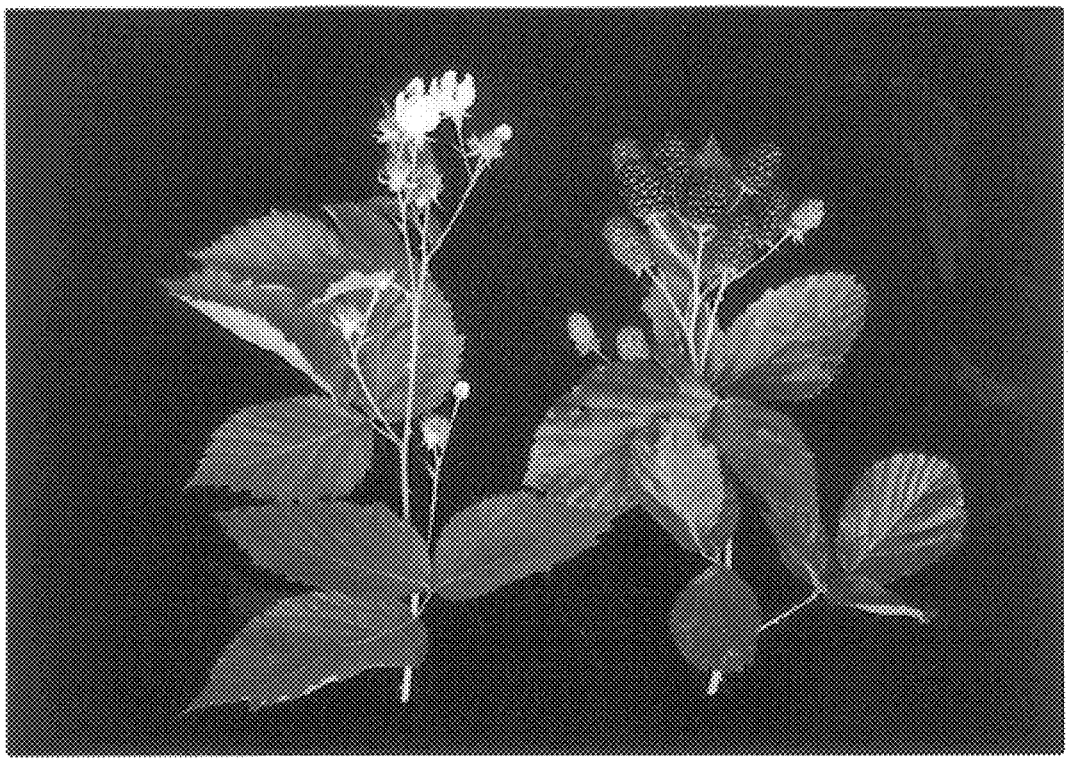
FIG. 3 is a photograph showing the flowering and fruiting laterals of 'Sleeping Beauty'.

The following detailed description of the new blackberry cultivar, 'Sleeping Beauty', is based upon recorded observations of plants two to five years old grown using commercial growing practices in Watsonville, Calif., and is believed to apply to plants of the 'Sleeping Beauty' cultivar grown in similar conditions of soil and climate elsewhere. Plants were planted on soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

5.1 CHARACTERISTICS OF THE NEW VARIETY

Table 1 provides information on the plant and fruit characteristics of the new blackberry cultivar 'Sleeping Beauty' compared with characteristics of the unpatented blackberry cultivars 'Olallie' and 'Chester'. Both 'Olallie' and 'Chester' are currently important cultivars for fresh market shipping, and thus are comparable to the proposed use of the new invention, 'Sleeping Beauty'. Observations of 'Sleeping Beauty' and 'Olallie' and 'Chester' were taken in side-by-side comparison in 1999 and 2000.

The new blackberry cultivar is particularly characterized and distinguished from other cultivars by its low chill requirement and its long fruiting cycle. Canes of 'Sleeping Beauty' are vigorous and thorny. The average cane length for 'Sleeping Beauty' under a normal growing season is 10.5 feet in comparison to the average cane length for 'Chester' which is 9 feet in a normal growing season. The primocane color for 'Sleeping Beauty' on the exposed side of the cane is 146B and 146C on the shaded side. Floricanes of 'Sleeping Beauty' are 146B on the exposed side and 146B on the shaded sided.

The leaves of 'Sleeping Beauty' have very minor undulations between where the veins are and are nearly flat. The leaf surface of 'Sleeping Beauty' is characterized by a few small, soft hairs on both the upper and lower leaf surface. The petiole color of 'Sleeping Beauty' is 146B when exposed to full sun. The bud break of 'Sleeping Beauty' is in late March and usually 1–2 weeks before 'Olallie'. The petal color is 155C. The pedicel length of 'Sleeping Beauty' averages 19 mm under normal growing conditions and the sepal color is 143A.

The fruit color of 'Sleeping Beauty' is black with moderate amount of post harvest drupelet color reversion. The fruit is large with a slightly tart flavor. Postharvest fruit rot resistance is average in comparisons with many selections and varieties. The fruit yield of 'Sleeping Beauty' is moderately high, averaging around 23,000 lbs per acre in comparison to the fruit yield of 'Olallie' which averages around 21,000 lbs per acre.

'Sleeping Beauty' is distinguished from its pollen parent, 'Hull Thornless', by being thorny, having a more upright growth habit, and having larger fruit. Additionally, 'Sleeping Beauty' has a much lower chill requirement and an earlier season than its pollen parent 'Hull Thornless'. 'Sleeping Beauty' is distinguished from its seed parent, 'Brazos', by having firmer and less acidic fruit.

TABLE 1

PLANT CHARACTERISTICS OF 'SLEEPING BEAUTY'

| | 'Sleeping Beauty' | 'Olallie' | 'Chester' |
|---|---|---|---|
| GENERAL | | | |
| Vigor | high | Moderate - high | high |

TABLE 1-continued

PLANT CHARACTERISTICS OF 'SLEEPING BEAUTY'

| | 'Sleeping Beauty' | 'Olallie' | 'Chester' |
|---|---|---|---|
| Growth habit | upright | trailing | semi-upright |
| Productivity | moderately high | high | high |
| Self fruitfulness | yes | yes | yes |
| Number of young shoots | many | medium | medium |
| CANES | | | |
| Primocanes | | | |
| Anthocyanin coloration | absent | present | present |
| Spines | present | present | absent |
| color | green | purple | — |
| attitude of tip | horizontal to downward | horizontal | — |
| texture | rigid | heavy | — |
| presence and distribution on petioles | present; irregularly distributed | present; irregularly distributed | absent |
| density in central third of shoot | medium | medium | — |
| Internodal distance (cm) - central third of mature cane | 3.3 | 2.6 | 3.1 |
| Glaucosity on full grown shoot | absent or very weak | weak | weak |
| Strength of full grown shoot | strong | medium | strong |
| Cane cross section | angular to grooved | rounded to angular | angular to grooved |
| LEAVES | | | |
| Relief between veins | weak | medium | medium |
| Number of leaflets | usually 5 | usually 3 | usually 5 |
| Leaf color | medium | medium | light |
| upper side | 139A | 137A, 137B | 147A |
| underside | 137C | 147B | 146A |
| Glossiness of upper surface | glossy | medium | dull |
| Leaf cross section | concave | concave-flat | concave |
| Terminal leaflet | | | |
| length (cm) | 9.5 | 8.9 | 11.1 |
| width (cm) | 6.5 | 7.6 | 9 |
| shape | ovate | cordate | cordate |
| tip | acuminate | acuminate | acuminate |
| base | rounded | cordate | cordate |
| margin | double serrate | double serrate | double serrate |
| Lateral leaflet | | | |
| overlap of lateral leaflets | touching | overlapping | overlapping |
| length (cm) | 9.1 | 8.7 | 10.2 |
| width (cm) | 5.4 | 6.1 | 7.1 |
| shape | ovate | ovate | ovate |
| tip | acute | acuminate | acute |
| base | acute | acute | acute |
| margin | double serrate | double serrate | serrate |
| Petiole | | | |
| mean length (cm) | 6.8 | 5.3 | 7.9 |
| range | 5.6–7.8 | 3.6–8.7 | 3.9–10.2 |
| pigmentation of upper surface | purplish red | green - slightly pink | purple |
| pigmentation of underside | some red, mostly green | green - slightly pink | green - pinkish |
| Length of stalklet | short | very short | medium |

TABLE 1-continued

PLANT CHARACTERISTICS OF 'SLEEPING BEAUTY'

| | 'Sleeping Beauty' | 'Olallie' | 'Chester' |
|---|---|---|---|
| Rachis length (cm) between terminal and adjacent lateral leaflets) | 2.9 | 2.8 | 3.1 |
| Stipule orientation | erect | variable; clasping to erect | erect |
| FLOWERS | | | |
| Time of bud burst | early | early | late |
| Time of beginning of flowering | early | early | late |
| Flower size | large | small to medium | small to medium |
| Petal size | | | |
| length (mm) | 20.1 | 16.5 | 18.3 |
| width (mm) | 16.5 | 11.7 | 10.9 |
| Anthocyanin color of pedicel | absent | absent | present |
| Intensity of pedicel coloration | — | — | weak |
| Length of pedicel | medium-long | long | short |
| Flower number (third node from tip of lateral) | 7.6 | 3.6 | 2 |
| FRUIT | | | |
| Harvest season | early to mid | early | mid to late |
| Dimensions | | | |
| weight (g/fruit) | 5.1 | 5.2 | 3.2 |
| size | medium | medium | small |
| length (cm) | 2.4 | 3.3 | 1.9 |
| width (cm) | 1.7 | 1.4 | 1.9 |
| Fruiting lateral length (in mid cane) | medium-long | medium | medium - long |
| mean number of fruit per lateral | 9.1 | 6.2 | 22.8 |
| range | 4–18 | 3–9 | 17–40 |
| Shape | elliptic longer than broad | narrow ovate much longer than broad | round to ovate as long as broad |
| Color | black | purple-black to black | black |
| immature | 187B | 178A - 183B | 184A |
| maturing | 200A | 187A | 200A - 202A |
| mature | 202A | 200A | 202A |
| Firmness | medium | medium | firm |
| Glossiness | medium strong | medium - strong | medium |
| Soluble solids | 10.2 | 9.7 | 9.9 |
| Titratable acidity (% as citric acid) (ml of added 0.1N NaOH to pH 8.1) | 10.2 | 13.3 | 9.9 |
| Number of drupelets per fruit | 94 | 86 | 40 |

Table 2 provides information on the seed weight of the new blackberry cultivar 'Sleeping Beauty' compared with characteristics of the blackberry cultivars 'Zorro' (application Ser. No. 09/772,327), 'Olallie' (non-patented), 'Chester' (non-patented), 'Pecos' (application Ser. No. 09/772,211), and 'Sonoma'.

TABLE 2

| Cultivar | Seed Weight |
|---|---|
| 'Zorro' | 2.3 mg |
| 'Olallie' | 2.1 mg |
| 'Chester' | 3.5 mg |
| 'Sleeping Beauty' | 4.1 mg |
| 'Pecos' | 3.5 mg |
| 'Sonoma' | 3.4 mg |

5.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531-5). Using a variety of oligonucleotide primers, along or in combination, RAPD analysis of 'Sleeping Beauty', 'Chester', and 'Olallie' yielded DNA fragment patterns that uniquely distinguish each of these genetically distinct genotypes.

We claim:

1. A new and distinct cultivar of blackberry plant, substantially as shown and described.

* * * * *